United States Patent
Tamura et al.

(10) Patent No.: US 8,198,471 B2
(45) Date of Patent: Jun. 12, 2012

(54) 2, 2'-BIS (DIALKYLPHOSPHINO) BIPHENYL COMPOUND, PRODUCTION METHOD THEREOF, AND METAL COMPLEX COMPRISING THE COMPOUND AS LIGAND

(75) Inventors: Ken Tamura, Tokyo (JP); Masashi Sugiya, Tokyo (JP); Tsuneo Imamoto, Chiba (JP)

(73) Assignee: Nippon Chemical Industrial Co., Ltd., Tokyo (JP)

( * ) Notice: Subject to any disclaimer, the term of this patent is extended or adjusted under 35 U.S.C. 154(b) by 228 days.

(21) Appl. No.: 12/719,252

(22) Filed: Mar. 8, 2010

(65) Prior Publication Data

US 2010/0234626 A1 Sep. 16, 2010

(30) Foreign Application Priority Data

Mar. 10, 2009 (JP) .................................. 2009-56990

(51) Int. Cl.
*C07F 15/00* (2006.01)
*C07F 9/02* (2006.01)

(52) U.S. Cl. .......................................... 556/21; 568/17

(58) Field of Classification Search .................... 556/21; 568/17

See application file for complete search history.

(56) References Cited

U.S. PATENT DOCUMENTS

| 5,852,212 A | * | 12/1998 | Broger et al. | ................. 562/602 |
| 6,194,593 B1 | | 2/2001 | Imamoto et al. | |
| 2007/0021610 A1 | | 1/2007 | Imamoto et al. | |

FOREIGN PATENT DOCUMENTS

| EP | 2030978 A1 | 3/2009 |
| JP | 55-61937 A | 5/1980 |
| JP | 2000-319288 A | 11/2000 |
| JP | 2001-253889 A | 9/2001 |
| JP | 2007-56007 A | 3/2007 |
| JP | 2007-320909 A | 12/2007 |
| WO | 2007/139176 A1 | 12/2007 |

* cited by examiner

*Primary Examiner* — Porfirio Nazario Gonzalez

(74) *Attorney, Agent, or Firm* — Westerman, Hattori, Daniels & Adrian, LLP

(57) ABSTRACT

A novel phosphine compound capable of forming a metal complex useful as a catalyst for various asymmetric synthesis reactions, a production method thereof, and a metal complex comprising the aforementioned compound as a ligand.

7 Claims, No Drawings

2,2'-BIS (DIALKYLPHOSPHINO) BIPHENYL COMPOUND, PRODUCTION METHOD THEREOF, AND METAL COMPLEX COMPRISING THE COMPOUND AS LIGAND

BACKGROUND OF THE INVENTION

1. Field of Invention

The present invention relates to a 2,2'-bis(dialkylphosphino)biphenyl compound and a production method thereof. The biphenyl compound can be used as a ligand of a metal complex useful as a catalyst for asymmetric synthesis or an anticancer agent. In addition, the present invention also relates to a metal complex comprising the aforementioned biphenyl compound as a ligand.

2. Description of the Related Art

An optically active phosphine ligand having an asymmetric center on a phosphorus atom plays an important role in a catalytic asymmetric synthesis reaction using a transition metal complex. As such optically active phosphine ligand having an asymmetric center on a phosphorus atom, a 1,2-bis(dialkylphosphino)benzene derivative has been proposed in Japanese Patent Laid-Open No. 2000-319288.

Japanese Patent Laid-Open No. 2007-56007 proposes a 2,3-bis(dialkylphosphino)pyrazine derivative. This pyrazine derivative is derived from a pyrazine skeleton, and thus it is characterized in that it has extremely high electron-attracting properties, thereby causing a low electron density of phosphorus atoms at the phosphine site. A metal complex comprising this pyrazine derivative as a ligand is effectively used as a catalyst for reactions, in which the above-mentioned characteristics of the derivative are utilized.

On the other hand, it has been known that a metal complex comprising an optically active phosphine ligand having an asymmetric center on a phosphorus atom is useful, not only as a catalyst for an asymmetric synthesis reaction, but also as an anticancer agent (see International Publication WO 2007/139176, for example).

The present invention provides a phosphine compound capable of forming a metal complex that is more useful than the case of using previously known phosphine ligand, a production method thereof, and a metal complex comprising the phosphine compound as a ligand.

SUMMARY OF THE INVENTION

The present invention provides a 2,2'-bis(dialkylphosphino)biphenyl compound represented by the general formula (A-1) below:

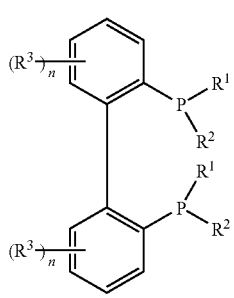

(A-1)

(wherein $R^1$ and $R^2$ each independently represent a substitutable alkyl group containing 1 to 10 carbon atoms; $R^3$ represents a monovalent substituent; and n represents an integer of 0 to 4).

In addition, the present invention provides a preferred method for producing the above described 2,2'-bis(dialkylphosphino)biphenyl compound, which comprises: subjecting a dialkyl(2-halogenophenyl)phosphine-borane compound represented by the general formula (A-2) below to a coupling reaction, so as to obtain a diphosphine-borane intermediate represented by the general formula (A-3) below; and then subjecting the diphosphine-borane intermediate to a deboranation reaction,

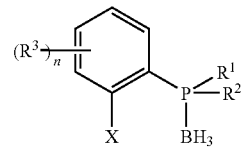

(A-2)

(wherein $R^1$, $R^2$, $R^3$, and n are the same as in the above general formula (A-1); and X represents a halogen atom),

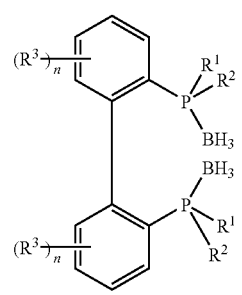

(A-3)

(wherein $R^1$, $R^2$, $R^3$, and n are the same as in the above general formula (A-1)).

Moreover, the present invention provides a metal complex comprising the above described 2,2'-bis(dialkylphosphino)biphenyl compound as a ligand.

According to the present invention, there can be provided a novel 2,2'-bis(dialkylphosphino)biphenyl compound capable of forming a metal complex that is useful as a catalyst for an asymmetric synthesis reaction or an anticancer agent. Moreover, according to the production method of the present invention, this biphenyl compound can be easily produced. Furthermore, a metal complex comprising this biphenyl compound as a ligand exhibits high enantioselectivity and high reaction activity when it is used as a catalyst for an asymmetric reaction, and thus it can be broadly applied to various types of asymmetric synthesis reactions.

DETAILED DESCRIPTION OF THE PREFERRED EMBODIMENTS

In the biphenyl compound of the present invention represented by the above described general formula (A-1), $R^1$ and $R^2$ each represent a substitutable alkyl group containing 1 to 10 carbon atoms. Two $R^1$s in the general formula (A-1) may be identical to or different from each other. The same applies to two $R^2$s. The alkyl group includes an acyclic alkyl group and an alicyclic alkyl group.

The acyclic alkyl group includes a linear alkyl group and a branched alkyl group. The linear alkyl group includes alkyl groups containing 1 to 10 carbon atoms, such as a methyl group, an ethyl group, an n-propyl group, an n-butyl group, an n-pentyl group, an n-hexyl group, and an n-heptyl group. The branched alkyl group includes alkyl groups containing 3 to 10 carbon atoms, such as an isopropyl group, an isobutyl group, a sec-butyl group, a tert-butyl group, an isoheptyl group, an isohexyl group, and a 1,1,3,3-tetramethylbutyl group.

The alicyclic alkyl group includes a monocyclic alkyl group and a polycyclic alkyl group. The monocyclic alkyl group includes alkyl groups containing 3 to 10 carbon atoms, such as a cyclopropyl group, a cyclobutyl group, a cyclopentyl group, and a cyclohexyl group. The polycyclic alkyl group includes alkyl groups containing 4 to 10 carbon atoms, such as an adamantyl group.

These alkyl groups may be substituted with at least one monovalent substituent, as appropriate. The substituent includes halogen atoms such as fluorine, chlorine, and bromine.

In the biphenyl compound of the present invention represented by the general formula (A-1), $R^3$ represents a monovalent substituent. When a plurality of $R^3$s are present, they may be identical to or different from one another. An example of the monovalent substituent represented by $R^3$ is an electron donating group. Specific examples of such electron-donating group include alkoxy groups such as a methoxy group, an ethoxy group and an isopropoxy group, and amino groups such as a dimethylamino group.

Another example of the monovalent substituent represented by $R^3$ is a substitutable alkyl group containing 1 to 6 carbon atoms. Specific examples of such alkyl group include alkyl groups containing 1 to 6 carbon atoms from among those exemplified as $R^1$ and $R^2$. These alkyl groups may also be substituted with at least one monovalent substituent, as appropriate. Such substituent includes those exemplified above as substituents for $R^1$ and $R^2$.

The biphenyl compound of the present invention represented by the above described general formula (A-1) includes: an optically active biphenyl compound having an asymmetric center on a phosphorus atom, which is represented by the general formula (1) below; a biphenyl compound exhibiting no optical activity, wherein $R^1$ and $R^2$ are identical to each other; and a biphenyl compound apparently exhibiting no optical activity because it is a racemic body, wherein $R^1$ and $R^2$ are different from each other though. Among others, the compound represented by the general formula (1) below exhibits excellent performance as a ligand of a metal complex used as a catalyst for asymmetric synthesis.

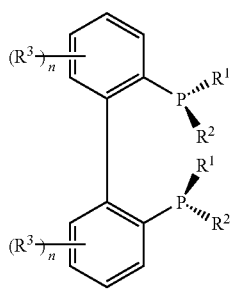

(1)

(wherein $R^1$ represents a substitutable alkyl group containing 2 to 10 carbon atoms; $R^2$ represents a substitutable alkyl group containing fewer carbon atoms than $R^1$; $R^3$ represents a monovalent substituent; and n represents an integer of 0 to 4).

In the general formula (1), in particular, $R^1$ is preferably a bulky substituent having steric hindrance. From this viewpoint, when $R^1$ is an acyclic alkyl group, a secondary alkyl group is preferable rather than a primary alkyl group, and a tertiary alkyl group is preferable rather than the secondary alkyl group. In addition, it is also preferable that $R^1$ be an alicyclic alkyl group. Preferred alkyl groups include a tert-butyl group and an adamantyl group.

On the other hand, in the general formula (1), $R^2$ represents a substitutable alkyl group having fewer carbon atoms than $R^1$. The difference between $R^1$ and $R^2$ in terms of the carbon number must be at least 1. When the biphenyl compound represented by the general formula (1) is used as a ligand of a metal complex that is used as a catalyst for asymmetric synthesis, a highly asymmetric space is formed. Taking into consideration this fact, it is preferable that there be a great difference between the steric hindrance of $R^1$ and that of $R^2$. That is to say, it is preferable that $R^1$ be a bulky substituent having steric hindrance, namely, a maximal group, whereas $R^2$ be a minimal group. Accordingly, a larger difference between $R^1$ and $R^2$ in terms of the carbon number is more preferable. Specifically, the difference between $R^1$ and $R^2$ in terms of the carbon number is preferably 2 or greater, particularly preferably 3 or greater, and further particularly preferably 4 or greater. If taking into consideration the fact that $R^2$ is a minimal group, $R^2$ is preferably an acyclic alkyl group, rather than an alicyclic alkyl group having the same carbon number. Further, among acyclic alkyl groups each having the same carbon number, a linear alkyl group is more preferable than a branched alkyl group. Finally, it can be said that the most preferred group as $R^2$ is a methyl group. However, in general, a group that can be used as $R^2$ is relatively determined based on the relationship with $R^1$. An example of a preferred combination of $R^1$ with $R^2$ is $R^1$ that is a tert-butyl group and $R^2$ that is a methyl group.

Moreover, $R^3$ in the general formula (1) is more preferably an electron-donating group. If $R^3$ is introduced into a biphenyl skeleton that does not have such $R^3$, the benzene ring of the biphenyl compound, and further, the electron density of phosphorus atoms, are changed. Thereby, when a metal complex produced from the biphenyl compound is used as a catalyst for asymmetric synthesis, reaction activity can be further increased. $R^3$ is generally introduced into a dialkylphosphino group at an ortho position and/or a para position, and preferably at a para position.

Particularly preferred specific examples of the biphenyl compound represented by the general formula (1) include the following compounds:

(R,R)-2,2'-bis(t-butylmethylphosphino)biphenyl,
(S,S)-2,2'-bis(t-butylmethylphosphino)biphenyl,
(R,R)-2,2'-bis(adamantylmethylphosphino)biphenyl,
(S,S)-2,2'-bis(adamantylmethylphosphino)biphenyl, (R,R)-2,2'-bis(1,1,3,3-tetramethylbutylmethylphosphino)biphenyl, and
(S,S)-2,2'-bis(1,1,3,3-tetramethylbutylmethylphosphino)biphenyl.

A preferred method for producing the 2,3-bis(dialkylphosphino)biphenyl compound of the present invention represented by the general formula (A-1) will be described below. It is to be noted that the biphenyl compound represented by the general formula (1) will be described below.

In the production method of the present invention, first, a dialkyl(2-halogenophenyl)phosphine-borane compound represented by the general formula (2) below is prepared:

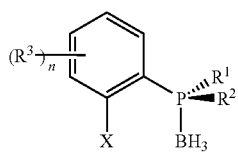

(wherein $R^1$, $R^2$, $R^3$, and n are the same as in the above general formula (1); and X represents a halogen atom).

Specific examples of the halogen atom represented by X in the general formula (2) include fluorine, chlorine, bromine, and iodine. The phosphine-borane compound represented by the general formula (2) can be synthesized according to the reaction formula (i) below, for example:

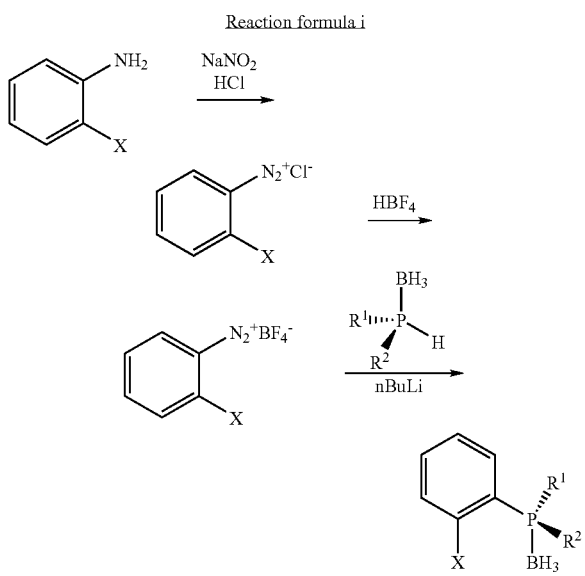

In the reaction formula (i), 2-halogenoaniline used as a starting substance is first diazotized to produce diazonium salts. A commercially available product can be used as such starting substance. The diazotization reaction can be carried out according to an ordinary method. The reaction is carried out in the presence of sodium nitrite, for example. Such diazonium salts can be isolated in the form of tetrafluoroborate. Subsequently, the obtained diazonium salts are allowed to react with dialkylphosphine-borane.

The dialkylphosphine-borane allowed to react with the diazonium salts can be prepared by a known method such as the method described in Japanese Patent Laid-Open No. 2001-253889. The dialkylphosphine-borane is deprotonated in an inactive solvent such as tetrahydrofuran. For such deprotonation, butyllithium is used, for example. The deprotonated dialkylphosphine-borane is allowed to act on the above-mentioned diazonium salts. This reaction rapidly progresses in an extremely low temperature environment or at a room temperature. As a result of this reaction, a phosphine-borane compound represented by the general formula (2) is generated in the reaction system.

It is to be noted that the phosphine-borane compound represented by the general formula (2), wherein n is 0 (namely, having no substituents $R^3$), is shown in the reaction formula (i). In the case of phosphine-borane compounds wherein n is an integer of 1 to 4 (namely, in the case of the phosphine-borane compounds having 1 to 4 substituents $R^3$), such $R^3$ can be easily introduced at the stage of the starting substance. Such $R^3$ can be introduced according to an ordinary method.

In the production method of the present invention, the phosphine-borane compound represented by the above-mentioned general formula (2) is subjected to a coupling reaction, so as to obtain a diphosphine-borane intermediate represented by the general formula (3) below:

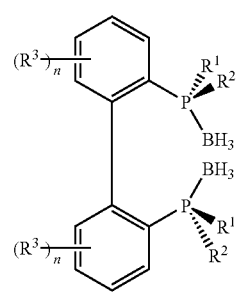

(wherein $R^1$, $R^2$, $R^3$, and n are the same as in the above general formula (1)).

The coupling reaction can be carried out, for example, by applying the conventionally known coupling reaction of a benzene compound using a copper compound. As a copper compound, copper chloride, copper bromide, or the like can be used. Such copper compound is generally used in an amount of 1 to 3 moles with respect to 1 mole of the phosphine-borane compound represented by the general formula (2). The coupling reaction is carried out, for example, in an organic solvent such as diethyl ether or tetrahydrofuran, in the presence of a base such as sec-butyllithium or n-butyllithium. The reaction time can be set at 1 to 50 hours. The reaction temperature can be set at −100° C. to 100° C.

Subsequently, the diphosphine-borane intermediate represented by the general formula (3) is subjected to a deboranation reaction, so as to obtain the biphenyl compound of the present invention represented by the general formula (1).

The deboranation reaction can be carried out, for example, in an organic solvent such as toluene, xylene or hexane, in the presence of a base such as 1,4-diazabicyclo[2.2.2]octane, N-methylmorpholine, triethylamine, pyrrolidine, or diethylamine. The reaction can be set at 1 to 24 hours. The reaction temperature can be set at 0° C. to 100° C.

Hereinbefore, a preferred method for producing the 2,3-bis(dialkylphosphino)biphenyl compound of the present invention was explained using the biphenyl compound represented by the general formula (1). In accordance with the above explanation, the compound represented by the general formula (A-2) is used instead of the compound represented by the general formula (2), and obtained intermediate represented by the general formula (A-3) is then subjected to the above described routines, so that the biphenyl compound of the present invention represented by the general formula (A-1) can be obtained.

The biphenyl compound of the present invention represented by the general formula (A-1) can be used as a ligand, together with a transition metal, to form a complex. A metal complex comprising the compound represented by the general formula (1) as a ligand, from among the biphenyl compounds of the present invention, is useful as a catalyst for asymmetric synthesis. Examples of such asymmetric synthesis include an asymmetric hydrogenation reaction, an asymmetric 1,4-addition reaction of organic boronic acid to electron-deficient olefin, an asymmetric hydrosilylation reaction, and an asymmetric Michael reaction.

The biphenyl compound represented by the general formula (1) has an asymmetric center on the phosphorus atom at a phosphine site owned by each of the two benzene rings of a biphenyl skeleton. Furthermore, the biphenyl compound has a factor of axial asymmetry, such that the rotation of a single bond between phenyl groups is limited by steric hindrance caused by a bulky dialkylphosphino group. Thus, the biphenyl compound represented by the general formula (1) is characterized in that it has an asymmetric center on a phosphorus atom, and also in that it has an axial asymmetric factor. By such characteristics, the use of a transition metal complex having the aforementioned biphenyl compound as a ligand is able to realize high enantioselectivity. In contrast, the conventionally known phosphine compound used as a ligand of a catalyst for asymmetric synthesis (please see Patent Documents 1 and 2, for example) has only an asymmetric center on a phosphorus atom, and it does not have such axial asymmetric factor. BINAP having a binaphthyl skeleton has been widely known as a ligand used for an asymmetric hydrogenation catalyst (please see Japanese Patent Laid-Open No. 55-61937, for example). This BINAP is an axially asymmetric substance, but it does not have an asymmetric center on a phosphorus atom.

Because of biphenyl skeleton, the biphenyl compound represented by the general formula (1) becomes highly rigid, and an included angle formed between the two phosphine sites and the transition metal becomes large. As a result, if a transition metal complex having the aforementioned biphenyl compound as a ligand is used as a catalyst, reductive elimination can be easily promoted.

In addition, the biphenyl compound represented by the general formula (1) may have a substituent $R^3$ on the biphenyl skeleton. According to the production method of the present invention, various types of $R^3$s can be easily introduced. An appropriate $R^3$ is introduced depending on a substrate used in the asymmetric synthesis reaction, so that the electric density of benzene rings and phosphorus atoms can be changed in the biphenyl compound, thereby controlling the biphenyl compound such that it exhibits adequate catalytic activity when used as a catalyst for asymmetric synthesis. Thereby, a metal complex having the biphenyl compound represented by the general formula (1) as a ligand can be applied to a wide range of asymmetric synthesis reactions.

Examples of a transition metal capable of forming a complex include rhodium, ruthenium, iridium, palladium, nickel, and iron. A preferred metal is rhodium. As a method for forming a complex from rhodium and the 2,3-bis(dialkylphosphino)biphenyl compound represented by the general formula (A-1), which is used as a ligand, the method described in *Jikken Kagaku Koza* (Experimental Chemistry Course), $4^{th}$ edition (edited by the Chemical Society of Japan, published by Maruzen Co., Ltd., Vol. 18, pp. 327-353) may be applied, for example. Specifically, the 2,3-bis(dialkylphosphino)biphenyl compound represented by the general formula (1) is allowed to react with bis(cycloocta-1,5-diene)rhodium tetrafluoroborate to produce a rhodium complex.

The thus obtained rhodium complex will be specifically exemplified below. It is to be noted that the number (1) represents the biphenyl compound represented by the general formula (1), the term "cod" represents 1,5-cyclooctadiene, and the term "nbd" represents norbornadiene.
[Rh((S,S)-(1))(cod)]$BF_4$, [Rh((R,R)-(1))(cod)]$BF_4$, [Rh((S,S)-(1))(nbd)]$BF_4$, [Rh((R,R)-(1)(nbd)]$BF_4$, [Rh((S,S)-(1))(cod)]$PF_6$, and [Rh((R,R)-(1))(cod)]$PF_6$.

Moreover, a metal complex formed from the biphenyl compound of the present invention represented by the above-mentioned general formula (A-1) used as a ligand and a transition metal atom selected from the group consisting of gold, silver and copper (preferably, gold) is also useful as an anticancer agent. When the biphenyl compound of the present invention is represented by L, this metal complex is represented by $[ML_2]^+X^-$.

The type of cancer, to which an anticancer agent comprising the biphenyl compound of the present invention as a ligand can be applied, is not particularly limited. Examples of such cancer include malignant melanoma, malignant lymphoma, digestive system cancer, lung cancer, esophageal cancer, stomach cancer, large bowel cancer, rectal cancer, colon cancer, ureteral tumor, gallbladder cancer, cholangiocarcinoma, biliary tract cancer, breast cancer, liver cancer, pancreatic cancer, testicular tumor, cancer of the upper jaw, tongue cancer, lip cancer, oral cavity cancer, pharyngeal cancer, laryngeal cancer, ovarian cancer, uterine cancer, prostatic cancer, thyroid cancer, cerebral tumor, Kaposi's sarcoma, angioma, leukemia, polycythemia vera, neuroblastoma, retinoblastoma, myeloma, ladder tumor, sarcoma, osteosarcoma, myosarcoma, skin cancer, basal cell cancer, skin appendage carcinoma, cancer caused by cutaneous metastasis, and cutaneous melanoma. In addition, this anticancer agent can be applied not only to malignant tumors, but also to benign tumors. Moreover, this anticancer agent can be used to suppress cancer metastasis, and in particular, it is useful as a cancer metastasis suppressing agent after surgery.

Such anticancer agent comprising the biphenyl compound of the present invention as a ligand can be administered in various forms to humans or non-human animals. As an administration route, any one of oral administration, injection into a vein or muscle, under or into the skin, etc., and parenteral administration such as intrarectal administration or transmucosal administration may be applied. Examples of a preparation form suitable for oral administration include a tablet, a pill, granules, powders, a capsule, a liquid agent, a suspending agent, an emulsifier, and a syrup. Examples of a pharmaceutical composition suitable for parenteral administration include an injection, drops, nasal drops, a spray, an inhaler, a suppository, and percutaneous absorption agents such as ointment, cream, powder embrocation, liquid embrocation or a skin patch. Further examples of such preparation form include an embedding pellet and a sustained preparation according to a known technique.

EXAMPLES

The present invention will be specifically described in the following examples. However, the examples are provided for illustrative purposes only, and are not intended to limit the scope of the present invention.

Production Example 1

Synthesis of (R)-2-(boranato(t-butyl)methylphosphino)bromobenzene

In accordance with the reaction formula below, (R)-2-(boranato(t-butyl)methylphosphino)bromobenzene was synthesized by the following procedures.

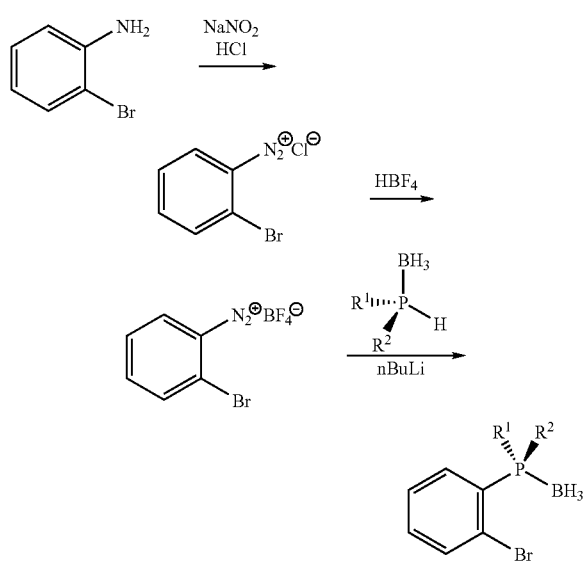

9.5 mL of concentrated hydrochloric acid, 65 mL of pure water, and 6.0 g (35 mmol) of 2-bromoaniline were added to a 200-mL four-necked flask, and they were then dissolved by heating. The obtained solution was cooled to 0° C. Thereafter, an aqueous solution of 2.46 g (35.1 mmol) of sodium nitrite that had previously been dissolved in 7.5 mL of pure water was added dropwise thereto over approximately 10 minutes. The reaction solution that was first in a gruel-like state was converted to a light yellow transparent liquid by stirring it for 30 minutes. Subsequently, 12.5 g (59.8 mmol) of a 42-mass-% $HBF_4$ aqueous solution was added dropwise thereto over approximately 5 minutes. As a result, light yellow crystals were immediately precipitated. The reaction solution was stirred for 30 minutes, and the crystals were then filtrated with a glass filter. The resultant was washed with 30 mL of pure water, and was then washed with a mixed solution of 8 mL of methanol and 32 mL of ether. Thereafter, the resultant was dried under a reduced pressure, so as to obtain 4.5 g of 2-bromobenzenediazonium tetrafluoroborate in the form of white crystals (yield: 48%).

2.36 mg (2.00 mmol) of (S)-t-butylmethylphosphine-borane was added to a well dried 30-mL Schlenk tube, followed by Ar substitution. Thereafter, 6 mL of dehydrated THF was added thereto, and it was then dissolved therein by stirring it. The obtained solution was cooled to −78° C., and 1.5 mL (2.4 mmol) of hexane solution of n-BuLi (1.6 mol/L) was slowly added to the solution. The obtained mixture was stirred for 20 minutes, and 650 mg (2.40 mmol) of the aforementioned 2-bromobenzenediazonium tetrafluoroborate was added in small amounts to the reaction solution. The temperature of a dark red-purple transparent solution was increased to a room temperature over 2 hours, and the solution was then stirred at the room temperature for 2 hours. A saline solution and ethyl acetate were added to the solution to separate an organic layer, and it was then washed with a saline solution. The resultant was dried over $MgSO_4$, and the solvent was then concentrated, followed by purification by silica gel chromatography, so as to obtain 60 mg of (R)-2-(boranato(t-butyl)methylphosphino)bromobenzene in the form of white crystals (yield: 11%). The analytical results of the obtained compound are shown below.

(Analytical Results)
Melting point; 90~92° C.
[α]25D-28.7 (c 0.515, $CHCl_3$)
$^1$H NMR (500 MHz, $CDCl_3$) δ: 0.20-1.05 (m, 3H), 1.19 (d, J=14.3 Hz, 9H), 1.91 (d, 9.7 Hz, 3H), 7.32 (t, 8.7 Hz, 1H), 7.40 (t, 7.5 Hz, 1H), 7.64 (d, 9.0 Hz, 1H), 8.06 (dd, 12.6,12.9 Hz, 1H)
$^{31}$P NMR (202 MHz, $CDCl_3$) δ: 38.3
APCI-MS: m/z 275, 273 ($M^+$+H)

Example 1

Synthesis of (R,R)-2,2'-bis(t-butylmethylphosphino)-1,1'-biphenyl

In accordance with the reaction formula below, (R,R)-2,2'-bis(t-butylmethylphosphino)-1,1'-biphenyl was synthesized by the following procedures.

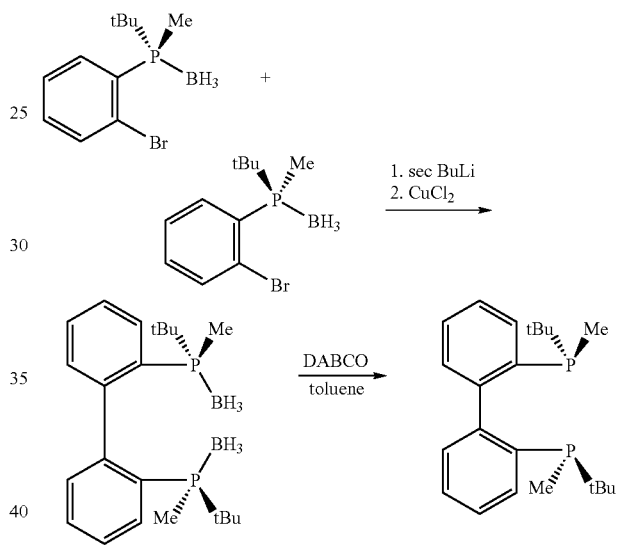

231 mg (0.85 mmol) of the (R)-2-(boranato(t-butyl)methylphosphino)bromobenzene obtained in Production Example 1 was added to a well dried 10-mL Schlenk tube, followed by Ar substitution. Thereafter, 4 mL of dehydrated tetrahydrofuran was added thereto, and it was then dissolved therein by stirring it. The obtained solution was cooled to −78° C., and 0.85 mL of hexane solution of sec-BuLi (1.0 mol/L) was slowly added to the solution. Thirty minutes later, 180 mg (1.34 mmol) of $CuCl_2$ was added to the solution, and the obtained mixture was then stirred for 30 minutes. Thereafter, the temperature of a brownish-red slurry solution was increased to a room temperature over 2 hours, and the solution was then stirred at the room temperature overnight. Thereafter, pure water was added to the reaction solution to terminate the reaction. Ether and a 28-mass-% ammonia water were added to the reaction solution for liquid separation. Ether was added to a water layer for separation, and the obtained organic layers were gathered and were then washed with pure water and a saline solution. The resultant was dried over $MgSO_4$, and the solvent was then concentrated, followed by purification by silica gel chromatography, so as to obtain 57 mg of (R,R)-2,2'-bis(boranato(t-butyl)methylphosphino)biphenyl in the form of colorless crystals (yield: 35%). The analytical results of the obtained compound are shown below.

(Analytical Results)

Melting point; 152~153° C.

$^1$H NMR (500 MHz, CDCl$_3$) δ: −0.70-0.40 (m, 6H), 1.07 (d, J=13.2 Hz, 18H), 1.67 (d, 8.9 Hz, 6H), 7.22-7.24 (m, 2H), 7.39-7.47 (m, 4H), 7.54-7.56 (m, 2H)

$^{31}$P NMR (202 MHz, CDCl$_3$) δ: 25.0

APCI-MS: m/z 386 (M$^-$)

39 mg (0.10 mmol) of the aforementioned (R,R)-2,2'-bis(boranato(t-butyl)methylphosphino)biphenyl and 33 mg (0.30 mmol) of 1,4-diazabicyclo[2.2.2]octane (DABCO) were added to a well dried 10-mL Schlenk tube, followed by Ar substitution. Thereafter, 0.5 mL of dehydrated toluene was added thereto, and it was then dissolved therein by stirring it. Subsequently, the obtained solution was stirred at 60° C. for 2 hours, and it was then confirmed by TLC that the raw materials had disappeared. Thereafter, the solution was concentrated. 3 mL of degassed hexane was added to the remaining white solid, and soluble components were then transferred into a Ar-substituted 20-mL Schlenk tube that had been prepared, separately. The same operation was carried out further several times, and the obtained hexane solution was then concentrated. The remaining white solid was recrystallized from methanol, so as to obtain 25 mg of (R,R)-2,2'-bis(t-butylmethylphosphino)biphenyl as a product of interest in the form of white crystals (yield: 70%). The analytical results of the obtained compound are shown below.

(Analytical Results)

Melting point; 106~108° C.

$^1$H NMR(500 MHz, CDCl$_3$) δ: 0.74 (m, 18H), 1.25 (s, 6H), 7.15 (m, 2H), 7.34 (m, 4H), 7.50 (m, 2H)

$^{31}$P NMR (202 MHz, CDCl$_3$) δ: −23.9

Example 2

Synthesis of (S,S)-(2,2'-bis(t-butylmethylphosphino)biphenyl)(1,5-cyclooctanediene)rhodium(I) tetrafluoroborate In accordance with the reaction formula below, (S,S)-(2,2'-bis(t-butylmethylphosphino)biphenyl)(1,5-cyclooctanediene)rhodium(I) tetrafluoroborate was synthesized by the following procedures.

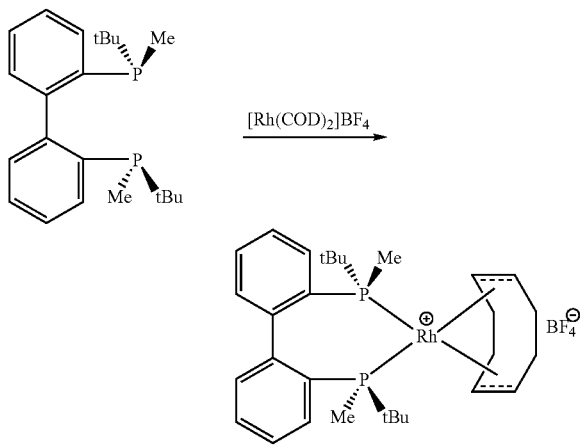

27.6 mg (0.077 mmol) of the (R,R)-2,2'-bis(t-butylmethylphosphino)biphenyl obtained in Example 1 and 28.4 mg (0.07 mmol) of [Rh(COD)$_2$]BF$_4$ were added, and thereafter, 0.5 mL of degassed THF was also added. The obtained mixture was stirred at a room temperature for 30 minutes, so that orange-colored crystals were precipitated. The solvent was concentrated, and 3 mL of ether was then added thereto, followed by filtration. The resultant was washed with a small amount of ether, and it was then dried under a reduced pressure, so as to obtain 42.3 mg of (S,S)-(2,2'-bis(t-butylmethylphosphino)biphenyl)(1,5-cyclooctanediene)rhodium(I) tetrafluoroborate in the form of orange-colored crystals (yield: 92%).

(Analytical Results)

$^1$H NMR (500 MHz, CDCl$_3$) δ: 0.84 (d, J=14.6 Hz, 18H), 1.65 (d, 6.0 Hz, 6H), 2.22-2.26 (m, 4H), 2.46-2.51 (m, 4H), 4.73-4.74 (m, 2H), 5.40-5.42 (m, 4H), 7.18-7.20 (m, 2H), 7.46-7.47 (m, 2H), 7.52-7.59 (m, 4H)

$^{31}$P NMR (202 MHz, CDCl$_3$) δ: 17.20 (d, 141 Hz)

Example 3

Asymmetric Reduction of Dehydroamino Acid

In accordance with the reaction formula below, the (S,S)-(2,2'-bis(t-butylmethylphosphino)biphenyl)(1,5-cyclooctanediene)rhodium(I) tetrafluoroborate obtained in Example 2 was used as an asymmetric hydrogenation catalyst, and the asymmetric reduction reaction of dehydroamino acid was carried out by the following procedures.

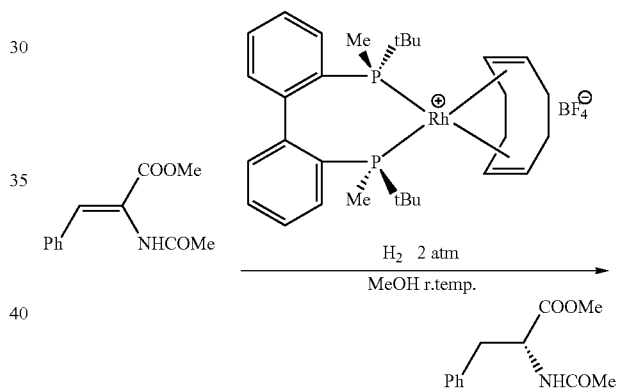

218 mg (0.994 mmol) of dehydroamino acid [2-(N-acetylamino)-3-phenyl-2-propene acid methyl ester] and 6.63 mg (0.001 mmol) of the (S,S)-(2,2'-bis(t-butylmethylphosphino)biphenyl)(1,5-cyclooctanediene)rhodium(I) tetrafluoroborate obtained in Example 2, which was to be used as an asymmetric hydrogenation catalyst, were added to a 100-mL glass autoclave. Nitrogen substitution was then carried out three times. Thereafter, 2 mL of dehydrated methanol that had previously been degassed was added to the resultant, and the mixture was then stirred for dissolution. Subsequently, hydrogen substitution was carried out five times. The hydrogen pressure was set at 2 atmospheric pressures, and the reaction was then initiated. As a result of the stirring of the solution at a room temperature for 2 hours, the consumption of hydrogen in the vessel was terminated. Thus, the reaction was terminated. The reaction solution was concentrated, and the remaining white crystals were then dissolved in ethyl acetate. The obtained solution was passed through a silica gel column. The obtained eluant was subjected to HPLC analysis. As a result, it was found that (R)-2-(N-acetylamino)-3-phenyl-2-propionic acid methyl ester was obtained at an enantiomeric excess (ee) of 93%. In addition, the aforementioned compound was analyzed by $^1$H NMR. As a result, the chemical yield was found to be 99% or more. The following conditions were applied to the HPLC analysis.

Daicel Chiralcel OJ, 1.0 mL/min, hexane: 2-propanol=9:1

The retention time of each enantiomer: (R form) $t_1$=13.3 min, (S form) $t_2$=19.3 min

What is claimed is:

1. A 2,2'-bis(dialkylphosphino)biphenyl compound, which is represented by the general formula (A-1) below:

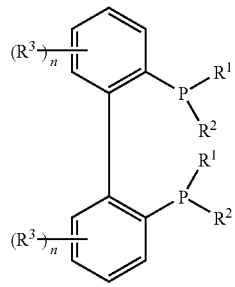

(A-1)

wherein $R^1$ represents a substitutable alkyl group containing 2 to 10 carbon atoms; $R^2$ represents a substitutable alkyl group containing fewer carbon atoms than $R^1$; $R^3$ represents a monovalent substituent; and n represents an integer of 0 to 4.

2. The 2,2'-bis(dialkylphosphino)biphenyl compound according to claim 1, which is represented by the general formula (1) beow:

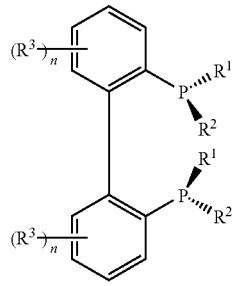

(1)

wherein $R^1$ represents a substitutable alkyl group containing 2 to 10 carbon atoms; $R^2$ represents a substitutable alkyl group containing fewer carbon atoms than $R^1$; $R^3$ represents a monovalent substituent; and n represents an integer of 0 to 4.

3. The 2,2'-bis(dialkylphosphino)biphenyl compound according to claim 2, wherein $R^1$ is a t-butyl group and $R^2$ is a methyl group.

4. A method for producing the 2,2'-bis(dialkylphosphino) biphenyl compound, which comprises:

subjecting a dialkyl(2-halogenophenyl)phosphine-borane compound represented by the general formula (A-2) below to a coupling reaction, so as to obtain a diphosphine-borane intermediate represented by the general formula (A-3) below; and subjecting the diphosphine-borane intermediate to a deboranation reaction:

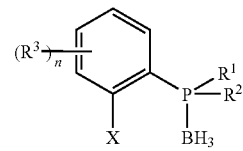

(A-2)

wherein $R^1$ and $R^2$ each independently represent a substitutable alkyl group containing 1 to 10 carbon atoms; $R^3$ represents a monovalent substituent; and n represents an integer of 0 to 4, and X represents a halogen atom,

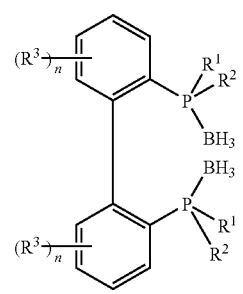

(A-3)

wherein $R^1$ and $R^2$ each independently represent a substitutable alkyl group containing 1 to 10 carbon atoms; $R^3$ represents a monovalent substituent; and n represents an integer of 0 to 4.

5. A method for producing the 2,2'-bis(dialkylphosphino) biphenyl compound according to claim 4, which comprises:

subjecting a dialkyl(2-halogenophenyl)phosphine-borane compound represented by the general formula (2) below to a coupling reaction, so as to obtain a diphosphine-borane intermediate represented by the general formula (3) below; and subjecting the diphosphine-borane intermediate to a deboranation reaction:

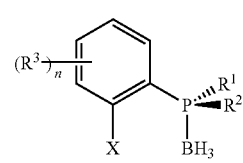

(2)

wherein $R^1$ and $R^2$ each independently represent a substitutable alkyl group containing 1 to 10 carbon atoms; $R^3$ represents a monovalent substituent; and n represents an integer of 0 to 4, and X represents a halogen atom,

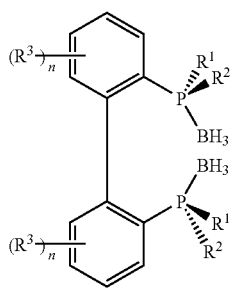

(3)

wherein $R^1$ and $R^2$ each independently represent a substitutable alkyl group containing 1 to 10 carbon atoms; $R^3$ represents a monovalent substituent; and n represents an integer of 0 to 4.

6. A metal complex, which comprises the 2,2'-bis(dialkylphosphino)biphenyl compound which is represented by the general formula (A-1) below:

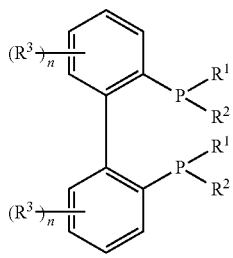

(A-1)

wherein $R^1$ represents a substitutable alkyl group containing 2 to 10 carbon atoms $R^2$ represents a substitutable alkyl group containing fewer carbon atoms than $R^1$; $R^3$ represents a monovalent substituent; and n represents an integer of 0 to 4.

7. The metal complex according to claim 6, wherein the 2,2'-bis(dialkylphosphino)biphenyl compound is the 2,2'-bis(dialkylphosphino)biphenyl compound which is represented by the general formula (1) below:

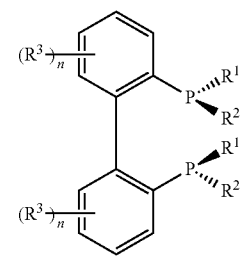

(1)

wherein $R^1$ represents a substitutable alkyl group containing 2 to 10 carbon atoms; $R^2$ represents a substitutable alkyl group containing fewer carbon atoms than $R^1$; $R^3$ represents a monovalent substituent; and n represents an integer of 0 to 4, and is used as a catalyst for asymmetric synthesis.

* * * * *